(12) United States Patent
Kunis

(10) Patent No.: US 9,526,572 B2
(45) Date of Patent: Dec. 27, 2016

(54) METHOD AND DEVICE FOR TREATMENT OF HYPERTENSION AND OTHER MALADIES

(75) Inventor: Christopher Gerard Kunis, Escondido, CA (US)

(73) Assignee: APERIAM MEDICAL, INC., Boise, ID (US)

( * ) Notice: Subject to any disclaimer, the term of this patent is extended or adjusted under 35 U.S.C. 154(b) by 0 days.

(21) Appl. No.: 13/457,033

(22) Filed: Apr. 26, 2012

(65) Prior Publication Data

US 2012/0277842 A1 Nov. 1, 2012

Related U.S. Application Data

(60) Provisional application No. 61/478,960, filed on Apr. 26, 2011.

(51) Int. Cl.
*A61F 2/84* (2006.01)
*A61B 18/14* (2006.01)
(Continued)

(52) U.S. Cl.
CPC ........... *A61B 18/1492* (2013.01); *A61B 18/02* (2013.01); *A61B 18/082* (2013.01);
(Continued)

(58) Field of Classification Search
CPC ............ A61B 17/320725; A61B 18/02; A61B 18/082; A61B 18/14; A61B 18/1492; A61B 2018/00267; A61B 2018/00404; A61B 2018/00434; A61B 2018/00494; A61B 2018/00511; A61B 2018/00577; A61B 2018/0212; A61B 2018/1435; A61F 2230/0091
(Continued)

(56) References Cited

U.S. PATENT DOCUMENTS 4,312,353 A 1/1982 Shahbabian
4,607,618 A 8/1986 Angelchik
(Continued)

FOREIGN PATENT DOCUMENTS

EP 0601338 A1 6/1994
EP 1406559 A1 4/2004
(Continued)

OTHER PUBLICATIONS

Markus P. Schlaich et al., "Renal Denervation as a Therapeutic Approach for Hypertension: Novel Implications for an Old Concept," Hypertension, 2009, vol. 54:1195-1201.
(Continued)

*Primary Examiner* — Julie A Szpira
(74) *Attorney, Agent, or Firm* — Michael R Shevlin

(57) ABSTRACT

Systems and methods for treating hypertension and other maladies are implemented using an implant device that is configured with one or more coils of ribbon which form ring-like structures when deployed in a patient's vasculature and are interconnected via respective extension arms formed from at least one helical winding. In an illustrative example, the catheter is positioned in the patient's aorta near the right angle junction with renal vasculature so that the axis of the catheter is substantially perpendicular to the axis of the vasculature. Through operation of an implant device delivery system having a pigtail distal end the ribbon emerges from the catheter tip and coils into the ring-like structures which deploy into the renal vasculature so that the longitudinal axes of the device and vasculature are substantially co-linear.

25 Claims, 16 Drawing Sheets

(51) Int. Cl.
*A61B 18/02* (2006.01)
*A61B 18/08* (2006.01)
*A61B 18/00* (2006.01)

(52) U.S. Cl.
CPC ............ *A61B 2018/00267* (2013.01); *A61B 2018/00404* (2013.01); *A61B 2018/00434* (2013.01); *A61B 2018/00494* (2013.01); *A61B 2018/00511* (2013.01); *A61B 2018/00577* (2013.01); *A61B 2018/0212* (2013.01); *A61B 2018/1435* (2013.01)

(58) Field of Classification Search
USPC ......... 606/200; 623/1.11, 1.15, 23.64, 23.65, 623/23.69, 23.7
See application file for complete search history.

(56) References Cited

U.S. PATENT DOCUMENTS

| | | | |
|---|---|---|---|
| 4,820,298 A * | 4/1989 | Leveen et al. ............... | 623/1.18 |
| 5,188,104 A | 2/1993 | Wernicke et al. | |
| 5,269,802 A | 12/1993 | Garber | |
| 5,342,348 A | 8/1994 | Kaplan | |
| 5,507,767 A | 4/1996 | Maeda et al. | |
| 5,551,427 A | 9/1996 | Altman | |
| 5,603,720 A | 2/1997 | Kieturakis | |
| 5,643,312 A | 7/1997 | Fischell et al. | |
| 5,653,734 A | 8/1997 | Alt | |
| 5,772,668 A | 6/1998 | Summers et al. | |
| 5,792,100 A | 8/1998 | Shantha | |
| 5,911,720 A | 6/1999 | Bourne et al. | |
| 6,019,779 A * | 2/2000 | Thorud et al. ................ | 606/198 |
| 6,126,673 A | 10/2000 | Kim et al. | |
| 6,129,685 A | 10/2000 | Howard, III | |
| 6,164,283 A | 12/2000 | Lesh | |
| 6,165,126 A | 12/2000 | Merzenich et al. | |
| 6,167,311 A | 12/2000 | Rezai | |
| 6,168,573 B1 | 1/2001 | Fielding et al. | |
| 6,176,242 B1 | 1/2001 | Rise | |
| 6,330,481 B1 | 12/2001 | Van Wijk et al. | |
| 6,375,666 B1 | 4/2002 | Mische | |
| 6,463,317 B1 | 10/2002 | Kucharczyk et al. | |
| 6,491,710 B2 * | 12/2002 | Satake ............................ | 606/191 |
| 6,500,174 B1 | 12/2002 | Maguire et al. | |
| 6,522,926 B1 | 2/2003 | Kieval et al. | |
| 6,607,520 B2 | 8/2003 | Keane | |
| 6,613,074 B1 * | 9/2003 | Mitelberg et al. ........... | 623/1.11 |
| 6,632,223 B1 * | 10/2003 | Keane ................ | A61B 18/1492 604/14 |
| 6,708,064 B2 | 3/2004 | Rezai | |
| 6,716,242 B1 | 4/2004 | Altman | |
| 6,764,498 B2 | 7/2004 | Mische | |
| 6,827,734 B2 | 12/2004 | Fariabi | |
| 6,978,174 B2 | 12/2005 | Gelfand et al. | |
| 6,986,784 B1 | 1/2006 | Weiser et al. | |
| 7,097,643 B2 | 8/2006 | Cornelius et al. | |
| 7,162,303 B2 | 1/2007 | Levin et al. | |
| 7,192,438 B2 | 3/2007 | Margolis | |
| 7,195,628 B2 | 3/2007 | Falkenberg | |
| 7,209,783 B2 | 4/2007 | Fellows et al. | |
| 7,266,414 B2 | 9/2007 | Cornelius et al. | |
| 7,300,449 B2 | 11/2007 | Mische | |
| 7,493,162 B2 | 2/2009 | Girouard et al. | |
| 7,520,893 B2 * | 4/2009 | Rivelli, Jr. ................... | 623/1.22 |
| 7,632,302 B2 | 12/2009 | Vreeman et al. | |
| 7,678,081 B2 | 3/2010 | Whiting et al. | |
| 7,727,229 B2 | 6/2010 | He et al. | |
| 7,837,676 B2 | 11/2010 | Sinelnikov et al. | |
| 7,850,685 B2 | 12/2010 | Kunis et al. | |
| 7,998,151 B2 | 8/2011 | St. Goar et al. | |
| 8,126,561 B2 * | 2/2012 | Chavan et al. ................ | 607/44 |
| 8,257,376 B2 | 9/2012 | Solem | |
| 2001/0005793 A1 * | 6/2001 | Brenneman ................... | 623/1.11 |
| 2001/0041890 A1 | 11/2001 | Hassett et al. | |
| 2002/0091434 A1 | 7/2002 | Chambers | |
| 2002/0111618 A1 | 8/2002 | Stewart et al. | |
| 2003/0018362 A1 | 1/2003 | Fellows et al. | |
| 2003/0055467 A1 | 3/2003 | Ben Haim et al. | |
| 2003/0055491 A1 | 3/2003 | Schwartz et al. | |
| 2003/0060858 A1 | 3/2003 | Kieval et al. | |
| 2004/0005295 A1 | 1/2004 | Lee et al. | |
| 2004/0106952 A1 | 6/2004 | Lafontaine | |
| 2004/0116965 A1 | 6/2004 | Falkenberg | |
| 2004/0133260 A1 | 7/2004 | Schwartz et al. | |
| 2004/0153139 A1 | 8/2004 | Altman | |
| 2004/0158313 A1 | 8/2004 | Altman | |
| 2004/0167598 A1 | 8/2004 | Margolis | |
| 2004/0172088 A1 | 9/2004 | Knudson et al. | |
| 2004/0181178 A1 | 9/2004 | Aldrich et al. | |
| 2004/0215180 A1 | 10/2004 | Starkebaum et al. | |
| 2004/0215186 A1 | 10/2004 | Cornelius et al. | |
| 2004/0215310 A1 * | 10/2004 | Amirana ....................... | 623/1.11 |
| 2004/0220655 A1 * | 11/2004 | Swanson et al. ............. | 623/1.11 |
| 2004/0243107 A1 | 12/2004 | Macoviak et al. | |
| 2004/0249443 A1 | 12/2004 | Shanley et al. | |
| 2004/0254597 A1 | 12/2004 | Schwartz et al. | |
| 2004/0260384 A1 | 12/2004 | Allen | |
| 2005/0080481 A1 * | 4/2005 | Madda et al. ................ | 623/1.22 |
| 2005/0090820 A1 | 4/2005 | Cornelius et al. | |
| 2005/0119647 A1 | 6/2005 | He et al. | |
| 2005/0131503 A1 | 6/2005 | Solem | |
| 2005/0149164 A1 * | 7/2005 | Rivelli ......................... | 623/1.11 |
| 2005/0245957 A1 | 11/2005 | Starkebaum et al. | |
| 2006/0116666 A1 | 6/2006 | Cornelius et al. | |
| 2006/0178725 A1 | 8/2006 | Cornelius | |
| 2006/0241680 A1 * | 10/2006 | Johnson et al. .............. | 606/200 |
| 2006/0247607 A1 | 11/2006 | Cornelius et al. | |
| 2006/0247719 A1 | 11/2006 | Machino et al. | |
| 2006/0282120 A1 | 12/2006 | Sih | |
| 2007/0049866 A1 | 3/2007 | Schwartz et al. | |
| 2007/0067009 A1 | 3/2007 | Gandhi et al. | |
| 2007/0129746 A1 | 6/2007 | Mische | |
| 2007/0173921 A1 | 7/2007 | Wholey et al. | |
| 2008/0065180 A1 | 3/2008 | Dobak, III et al. | |
| 2008/0077174 A1 * | 3/2008 | Mische .................. | A61F 5/0089 606/198 |
| 2008/0208322 A1 | 8/2008 | Sandu | |
| 2008/0275424 A1 | 11/2008 | Doshi et al. | |
| 2008/0281312 A1 | 11/2008 | Werneth et al. | |
| 2008/0294088 A1 | 11/2008 | Solem et al. | |
| 2008/0312676 A1 | 12/2008 | Solem | |
| 2009/0012510 A1 | 1/2009 | Bertolero et al. | |
| 2009/0163941 A1 | 6/2009 | Solem et al. | |
| 2009/0171445 A1 | 7/2009 | Swanson et al. | |
| 2009/0177262 A1 | 7/2009 | Oberti et al. | |
| 2009/0209988 A1 | 8/2009 | Solem et al. | |
| 2009/0216221 A1 | 8/2009 | Davis et al. | |
| 2009/0264983 A1 | 10/2009 | Solem | |
| 2009/0281557 A1 | 11/2009 | Sander | |
| 2010/0016877 A1 | 1/2010 | Solem | |
| 2010/0049099 A1 | 2/2010 | Thapliyal et al. | |
| 2010/0113928 A1 | 5/2010 | Thapliyal et al. | |
| 2010/0125288 A1 | 5/2010 | Gelfand et al. | |
| 2010/0191232 A1 | 7/2010 | Boveda | |
| 2010/0211155 A1 | 8/2010 | Swanson et al. | |
| 2010/0305603 A1 | 12/2010 | Nielsen et al. | |
| 2011/0060327 A1 | 3/2011 | Pachon Mateos et al. | |
| 2011/0060331 A1 | 3/2011 | Ibrahim et al. | |
| 2011/0213408 A1 | 9/2011 | Gross et al. | |
| 2011/0263921 A1 * | 10/2011 | Vrba ..................... | A61B 18/18 600/3 |
| 2011/0264116 A1 | 10/2011 | Kocur et al. | |
| 2011/0264166 A1 | 10/2011 | Benabid et al. | |
| 2011/0282343 A1 | 11/2011 | Kunis | |

FOREIGN PATENT DOCUMENTS

| | | |
|---|---|---|
| EP | 1605866 A2 | 12/2005 |
| EP | 1694246 A1 | 8/2006 |
| EP | 1809195 A2 | 7/2007 |
| EP | 1881804 A1 | 1/2008 |
| WO | 0126585 A1 | 4/2001 |
| WO | 03/097159 A1 | 11/2003 |

(56) References Cited

FOREIGN PATENT DOCUMENTS

| WO | 2008154033 A1 | 12/2008 |
| WO | 2009027061 A1 | 3/2009 |
| WO | 2009/049677 A1 | 4/2009 |
| WO | WO 2012/130337 | 10/2012 |
| WO | WO 2012/131107 | 10/2012 |

OTHER PUBLICATIONS

Hans Mische, U.S. Appl. No. 09/444,273, filed Nov. 19, 1999.
Stoeckel et al., "Self-Expanding Nitinol Stents—Material and Design Considerations", European Radiology, Nitinol Devises & Components, pp. 1-12, 2003.

* cited by examiner

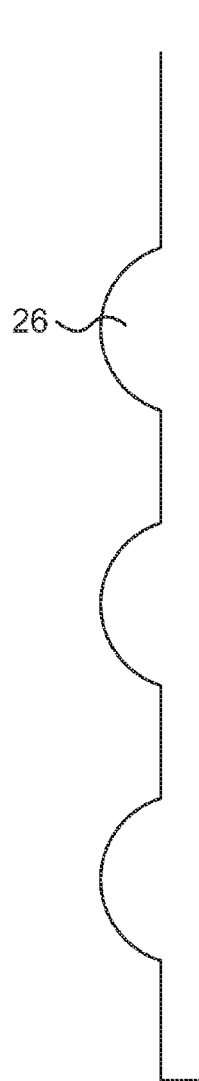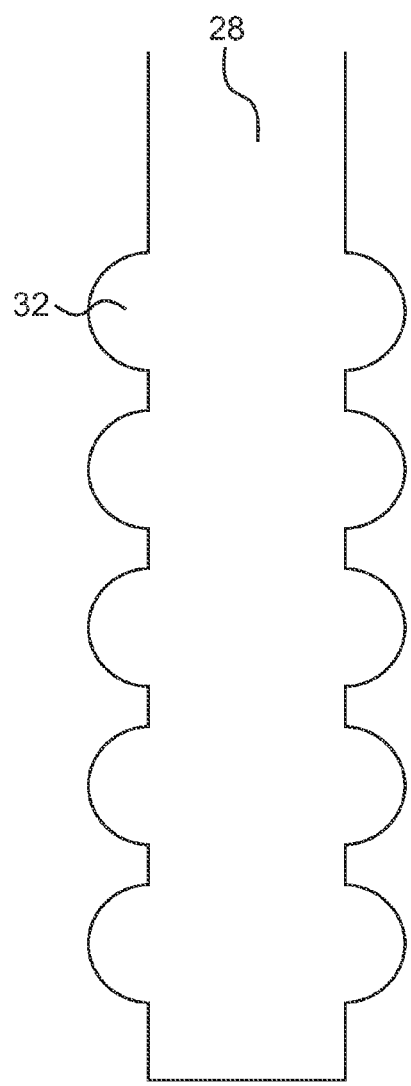
FIG. 4(A) FIG. 4(B)
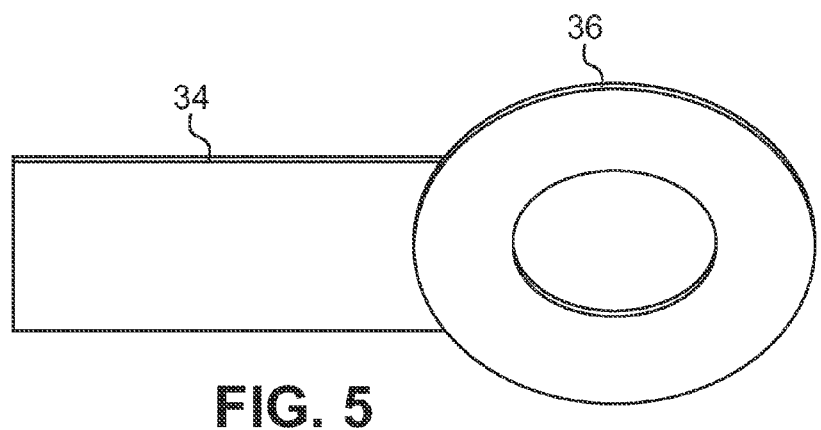
FIG. 5

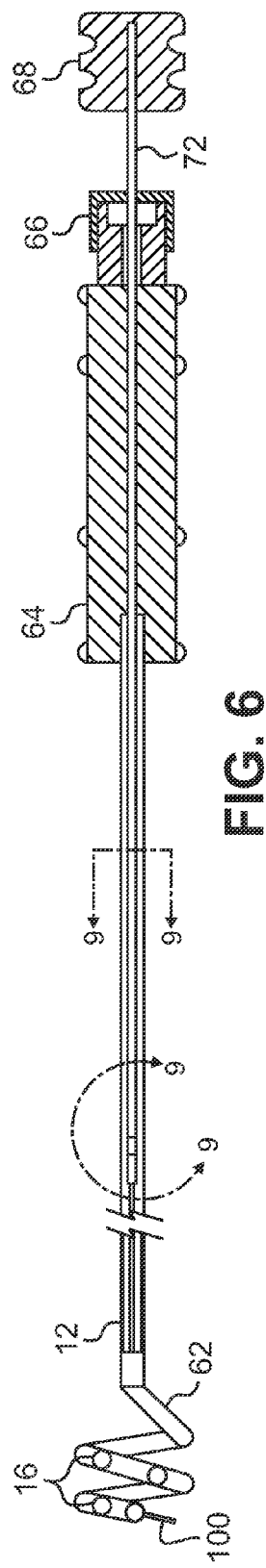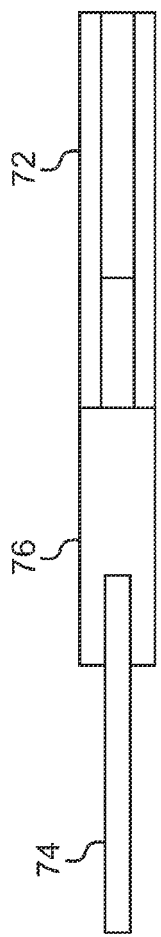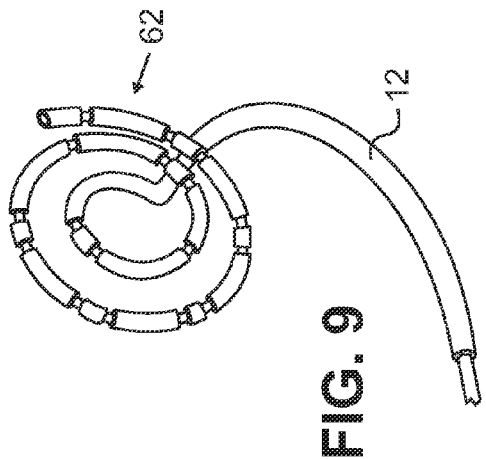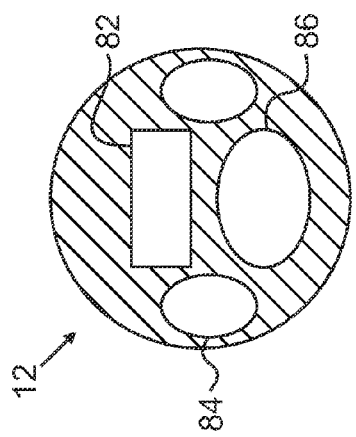

METHOD AND DEVICE FOR TREATMENT OF HYPERTENSION AND OTHER MALADIES

CROSS-REFERENCE TO RELATED APPLICATION

This application claims benefit of priority to U.S. Provisional Patent Application Ser. No. 61/478,960 filed Apr. 26, 2011 entitled "Method and Device for Treatment of Hypertension and Other Maladies" which is incorporated by reference herein in its entirety with the same effect as if set for at length.

BACKGROUND

Hypertension is a common and dangerous disease and represents a significant global health issue that continues to grow. Present treatments for hypertension typically include lifestyle changes, surgical procedures such as angioplasty, and various drug therapies which can be effective in some cases. However, the overall rate of control of hypertension and the therapeutic efforts to prevent progression of related maladies such as myocardial infarction, heart failure, chronic kidney disease, and diabetic nephropathy remain unsatisfactory and new treatment options are desirable.

This Background is provided to introduce a brief context for the Summary and Detailed Description that follow. This Background is not intended to be an aid in determining the scope of the claimed subject matter nor be viewed as limiting the claimed subject matter to implementations that solve any or all of the disadvantages or problems presented above.

SUMMARY

Systems and methods for treating hypertension and other maladies are implemented using an implant device that is configured with one, two, or more coils of ribbon which form ring-like structures when deployed in a patient's vasculature and, in the case of multiple rings or sets of coils, are interconnected via respective extension arms formed from at least one helical-shaped winding. In an illustrative example, a delivery catheter is positioned in the patient's aorta near the right angle junction with renal vasculature so that the axis of the catheter is substantially perpendicular to the axis of the vasculature. Through operation of an implant device delivery system having a pigtail distal end, the ribbon emerges from the catheter tip and coils into the ring-like structures which deploy into the renal vasculature so that the longitudinal axes of the device and vasculature are substantially co-linear.

In some implementations, the present systems and methods facilitate utilization of an implanted device that has an improved safety profile and which minimizes collateral damage over many current therapies. Therapy is delivered within the vessel having a focal tissue effect at the point of contact. Advantageously, no external energy source or capital investment is required for use with the implant device in many typical implementations. Methods utilized with the implant device need not directly integrate the device into the wall surface of the vessels. Rather, in an acute treatment, the implant device is designed and configured to apply and maintain radial or substantially radial force along the circumference of the vessels in which it is implanted, while employing a helical pattern of extension arms, connecting the two or more coils, each forming a ring-like structure. The radial force imparted from the implanted device is found to efficaciously block or retard sympathetic nerve communication to the kidneys which is identified as a principle contributor to the pathophysiology of hypertension, kidney disease, and heart failure. The implant device can be configured with multiple rings so that the radial force can be imparted along a target length of renal vasculature. The implant device may further be delivered using a procedure under only local anesthesia rather than requiring general anesthesia.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

DESCRIPTION OF THE DRAWINGS

FIGS. 4(A) and (B) illustrate features that may be employed in certain implementations of the implant device.

FIG. 5 illustrates a feature that may be employed in certain implementations of the implant device.

FIG. 6 illustrates details of a delivery device that may be employed to deliver the implant device.

FIG. 7 illustrates details of the device of FIG. 6.

FIG. 8 illustrates additional details of the device of FIG. 6.

FIG. 9 illustrates a perspective view of the device of FIG. 6.

Like reference numerals refer to like elements throughout. Elements are not drawn to scale unless otherwise indicated.

DETAILED DESCRIPTION

In some implementations, as described below, a ring system implant device as disclosed may be deployed in the renal vessels for the treatment of hypertension or diabetes. In particular, renal artery stenosis ("RAS"), or narrowing of one or both renal arteries, may lead to hypertension as the affected kidneys release renin to increase blood pressure to preserve perfusion to the kidneys. In the past, RAS was treated with the use of balloon angioplasty and stents, if necessary. However, the ring design as disclosed above may also be deployed in the renal arteries to treat RAS.

In this implementation, advantage may be taken of a delivery mechanism of even simpler design. In particular, if the ring system implant device is uncoiled and arranged in a delivery catheter or sheath in a substantially linear configuration, then upon deployment, the axis of the ring system will tend to be perpendicular to the axis of the catheter. Such a system is very desirable in a deployment in the renal vessels.

Figure 1:
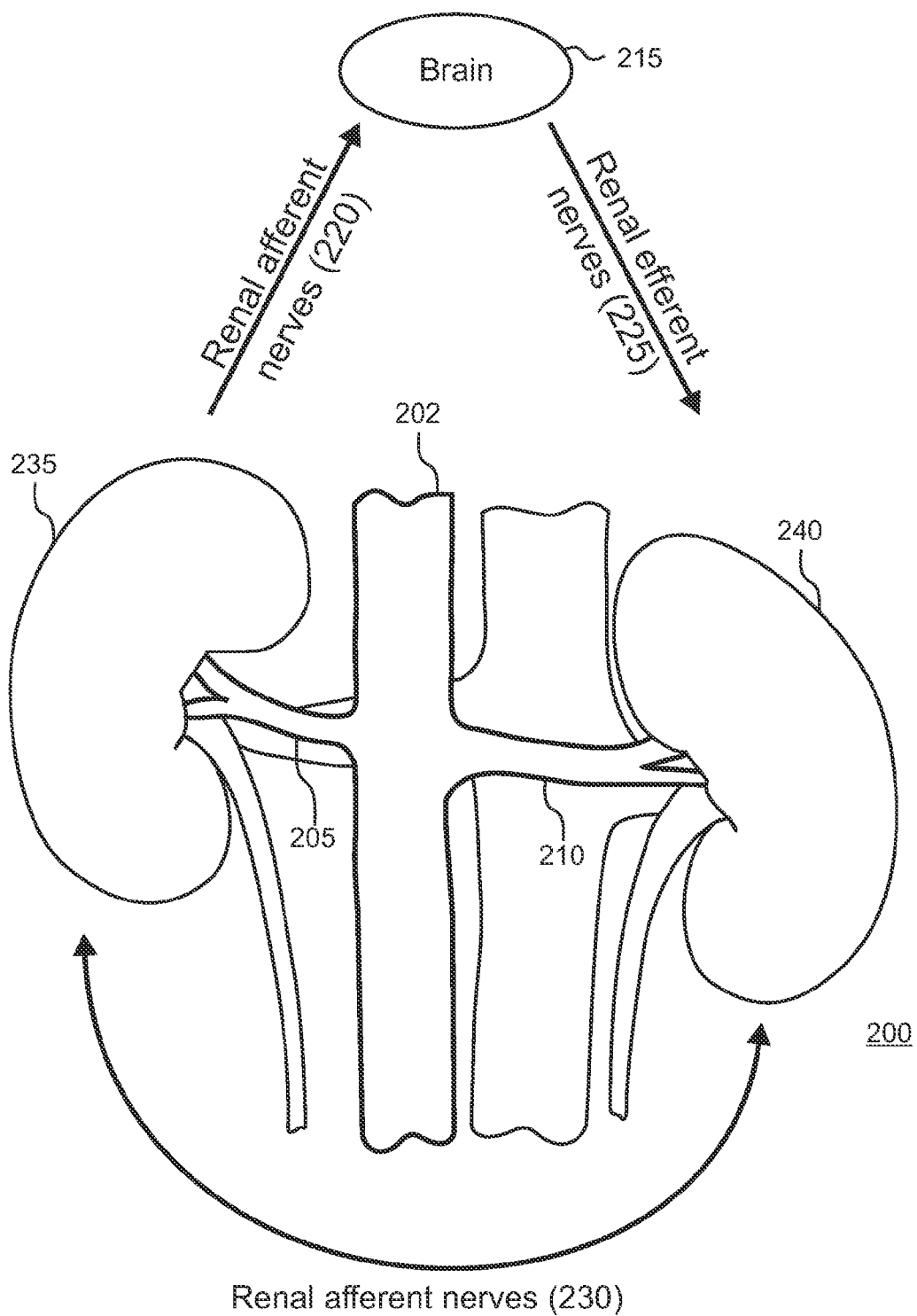
FIG. 1 shows an illustrative renal anatomy.
Figure 2:
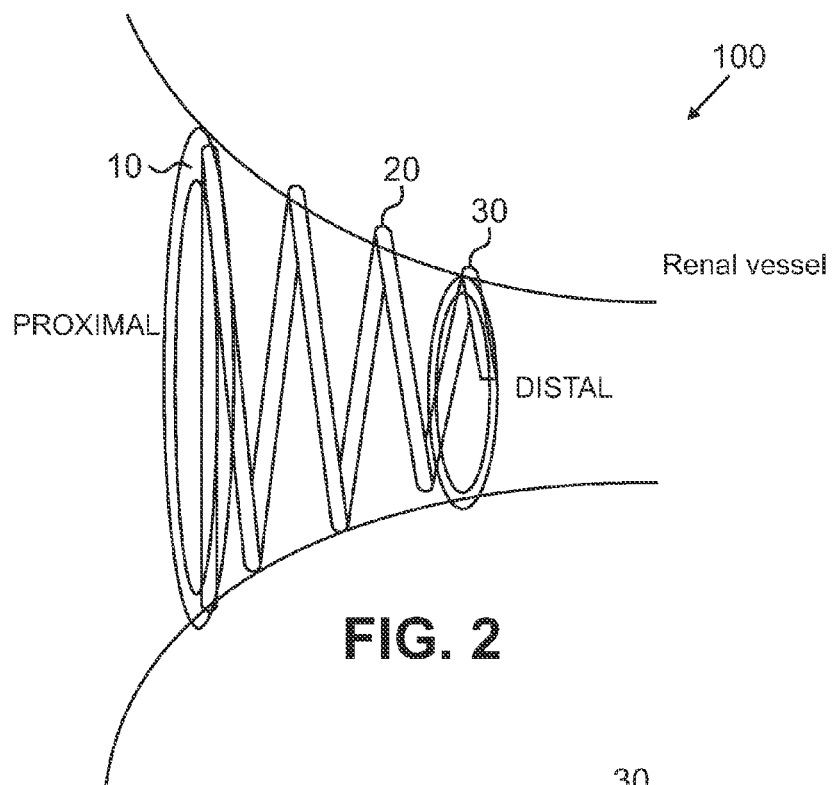
FIG. 2 schematically illustrates an implant device within a vessel, for example, a renal artery.

The renal anatomy 200 is illustrated in FIG. 1. As may be seen, a catheter deployed in the aorta 202 meets the renal arteries 205 and 210 at an angle approaching 90°. A ring system implant device emerging from the tip of the catheter having a longitudinal axis perpendicular to that of the catheter would be nearly substantially in proper position for delivery of therapy. Access to the renal arteries 205 and 210 may be gained via a catheter deployed from the femoral artery, as well as by other means. It is believed that the implant device would generally be installed at a location about ½ to ⅔rds of the distance into the renal artery, each of which is about 4 to 5 cm long. FIG. 1 also depicts a functional representation of the pathway between the renal anatomy 200 and the brain 215 with a system of renal afferent nerves 220 and renal efferent nerves 225, as well as a pathway with renal afferent nerves 230 between the kidneys 235 and 240.

Using the ring system implant device in this way, as well as in others, the implant device may confer a downstream neurological benefit as well as a cellular or electrical benefit. The delivery system for an implant device in the renal arteries would not necessarily require electrodes or other mapping devices on the delivery system in typical implementations.

Ring Details

Figure 3A:
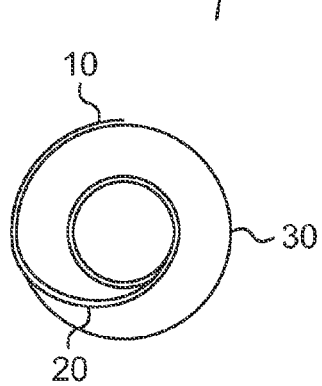
FIGS. 3(A)-(C) illustrate various views of the implant device of FIG. 1, with a single helix connecting two coils or rings.
Figure 3C:
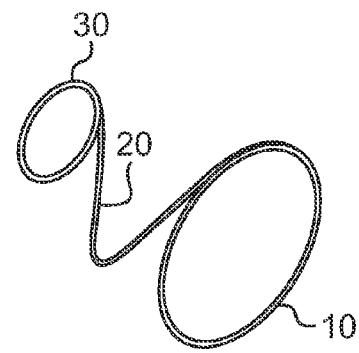
Figure 3B:
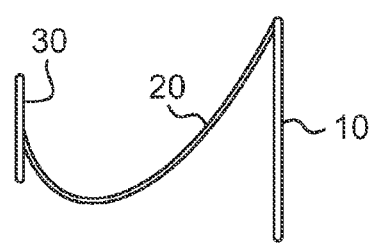
Figure 11A:
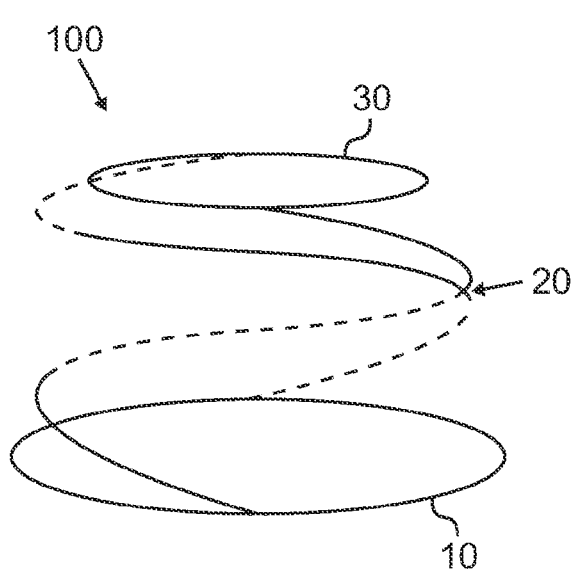
FIGS. 11(A)-(C) illustrate various views of another embodiment of the implant device, illustrating how two helices or a dual helix system may be employed to connect two coils or rings.
Figure 11B:
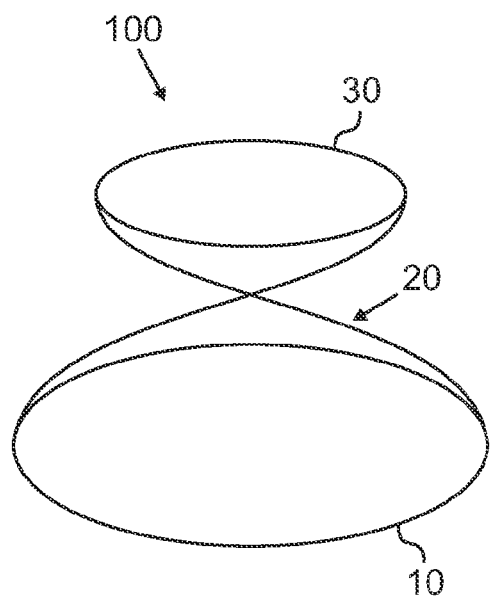
Figure 11:
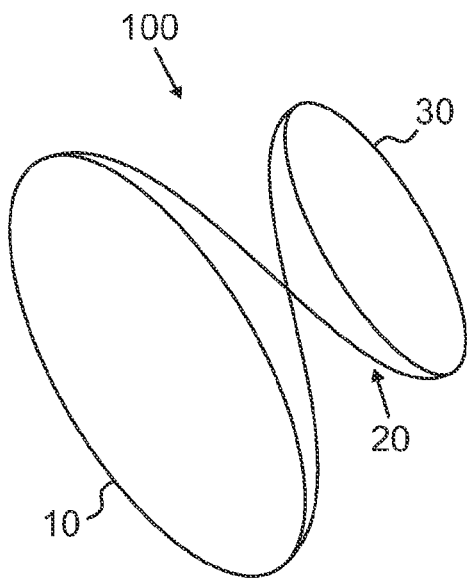

In one implementation, the implant device may include two or more separated rings that are connected by a single helical wire, a double helical wire, or a set of multiple helical wires. An exemplary implant device 100, in place within a renal vessel, is illustrated schematically in FIGS. 2 and 3(A)-(C). The implant device 100 includes a proximal ring 10 and a distal ring 30, which are separated by a helix or helical wind 20. FIGS. 3(A)-(C) illustrate various views of the implant device 100, where a single helical wind is employed between the proximal and distal rings. FIGS. 11(A)-11(C) illustrate various alternative exemplary implant devices 100, including those employing double helical arms or winds 20 between the distal ring 30 and proximal ring 10 of the implant device.

The diameter of the undeployed rings may be about 4 mm to 60 mm for the proximal ring, and about 6 mm to 60 mm for the distal ring. The diameter of the deployed rings may be about 2 mm to 40 mm for the proximal ring, and about 3 mm to 40 mm for the distal ring. The rings may be configured in a symmetrical pattern, for example, the diameter of the distal ring may be substantially equal to the diameter of the proximal ring. Alternatively, an asymmetric pattern may be employed having one end of the ring larger or smaller than the other end, for example, a distal end may have a 10 mm diameter while the proximal end may have a larger 25 mm diameter.

The size of the rings within a particular implant device can vary. For example, the diameter of each subsequent ring in a two-ring device may decrease in a distal direction. In some implementations, a distal ring may employ coils having a common diameter, while the proximal ring may employ coils having a decreasing diameter (decreasing in the distal direction).

The rings may be designed to deliver a force against the tissue of between about 5 g/mm$^2$ and 340 g/mm$^2$, for example, between about 20 g/mm$^2$ and 200 g/mm$^2$. The distal ring may provide a greater amount of force than the proximal one. Implant devices may be efficacious when configured to deliver a pressure of between about 0.01 to 0.20 N/mm$^2$ in a cylinder or vessel sized from 10 to 25 mm. More specifically, for smaller diameters, pressures may be from about 0.07 to 0.20 N/mm$^2$; for intermediate diameters, 0.03 to 0.05; and for larger diameters, 0.01 to 0.08. The overall force delivered to the vessel may be between about 1 to 9 N for a 15×15 device, 0.2 to 8 N for a 20×20 device, 0.3 to 7 N for a 25×25 device, and 1 to 5 N for a 30×30 device, although it will be understood that these values may vary with the size of the implant device, including the thickness of the ribbon. Typical values found appropriate are from 0.2 to 10 N, in particular 0.3 to 6 N. In tests, implanting intermediate sized devices (e.g., 27 mm diameter devices in a 19 mm vessel) resulted in the vessel extending to about 23 mm. Similar percentage increases may be expected for other size devices.

It is believed that the amount of pressure necessary should be more than 10 g/mm$^2$, for example, greater than 20 g/mm2, but less than 340 g/mm2, for example less than 200 g/mm2, as noted above. While it may be desirable to have the rings and helices exert a relatively constant force about the circumference of the vasculature, it is more likely given anatomical imperfections, that certain areas will receive more pressure than others. However, compliance of the rings and use of the helix helps to distribute forces around the implant device. In general, it is believed that the amount of pressure needed will primarily be a function of the material used, the diameter of the vasculature, and the thickness of the associated muscle sleeve.

One or more of the helices may revolve around a central axis 1, 1.5, or more times. In this way, even when placed in larger vessels, the available expansion room may cause an effective pressure block to be achieved. However, in this regard, it is noted that radial force decreases dramatically as the radius increases.

For implant devices made from ribbon wires, exemplary values of the ribbon width may be, for example, 1 to 2 mm, and between 0.5 and 2.5 mm. For coverage of greater portions of the renal vasculature, as may be appropriate for greater nerve coverage and thus denervation, the ribbon width may be made significantly wider, e.g., 5, 7, 10 mm, as well as other values. The overall length would likewise be greater, e.g., 1-4 or 5 cm overall.

To ensure a minimum of migration, the ends of the wire or ribbon forming the ring system may be scalloped or have another shape to increase frictional or mechanical resistance against movement. Such shapes are illustrated in FIGS. 4(A) and 4(B). In FIG. 4(A), a distal end 24 includes scallops or ribs 26, while in FIG. 4(B), the distal end 28 includes smaller but more frequent scallops or ribs 32. In addition, the external surface of the implant device 100 may have a textured surface, or may include a polymer sleeve, or a combination of the two, to further aid the device in fixation of the vessel. The polymer sleeve may also include a microcircuit to wirelessly enable electric rim interpretation during and after the procedure. Furthermore, a coating or biological agent of the implant surface may be employed to further reduce migration and/or erosion of the implant device.

Referring to FIG. 5, a distal end 34 of the wire or ribbon may further include a club shape 36 so as to minimize the chance of perforation. The hole in the club-shaped end may be employed to allow two implant devices to be attached to each other. In this way, multiple implant devices may be loaded into a delivery system to allow multiple installations in a single procedure. The implant devices may be attached end-to-end in a way akin to staples or railcars.

Deployment

The implant device may be deployed in various ways. In one implementation, illustrated in FIGS. 6-9, a delivery catheter 12 has a handle 64 for steerability and a knob 68 to control a pusher 72, for example, a flexible wire or elongated spring, at a proximal end. At a distal end, the delivery catheter may have a PeBax® (or other material) loop or pigtail 62. As shown in detail in FIG. 7, the pusher with a tip 76 extends through the delivery catheter 12, and the same is attached to an implant device 100 at a point within the catheter. The implant device 100 is uncoiled in this undeployed configuration, and the implant device may extend through the pigtail 62 and may further extend a short distance from the distal end of the pigtail during deployment. The distal end of the delivery system may also include a design where the catheter distal end is in a straight or neutral position and then steered using knobs and/or levers on the handle to create the pigtail distal segment. Another lever located on the handle may be employed to deflect or steer the distal segment for cannulation of each vessel.

By pushing the implant device out of the distal end of the catheter, shown in more detail in FIG. 7, the same may take up a position within the renal vessel as desired. One purpose of the PeBax pigtail is to protect the vessel during deployment in the same way that, for example, a Lasso® catheter does. In addition, it is noted that certain PeBax pigtails may be equipped with electrodes 16 for various purposes, as shown in FIGS. 6, 8, and 9. For example, selective electrode activation may be employed to ablate desired tissue to further enhance the efficacy of renal denervation provided by the implant device through application of heat or RF (radio frequency) emissions. Alternatively, instead of ablating the tissue with elevated temperatures, the pigtail may be adapted to deliver low temperatures via cryothermia therapy. The implant device may also be adapted to deliver thermal energy to selected tissue portions through inductive heating. The pitch of the distal loop or pigtail may be altered in a known manner, for example, by a control wire, to allow different geometries to be accommodated. FIG. 6 also illustrates element 66, which along with elements 74 and 76 of FIG. 10(A) may constitute Tuohy-Borst hemostasis valves or adaptors.

Referring to FIG. 8, a rectangular lumen 82 may be employed to contain and deliver the implant device. In addition, it will be understood that more than one rectangular or circular lumen may be employed, and their shapes may differ, according to the needs of any given catheter design, such as an oval lumen 86, as shown. In systems where the catheter is made fully steerable or deflectable, additional lumens 84 may be employed to provide the necessary control wires for steering or deflection.

Figure 10A:
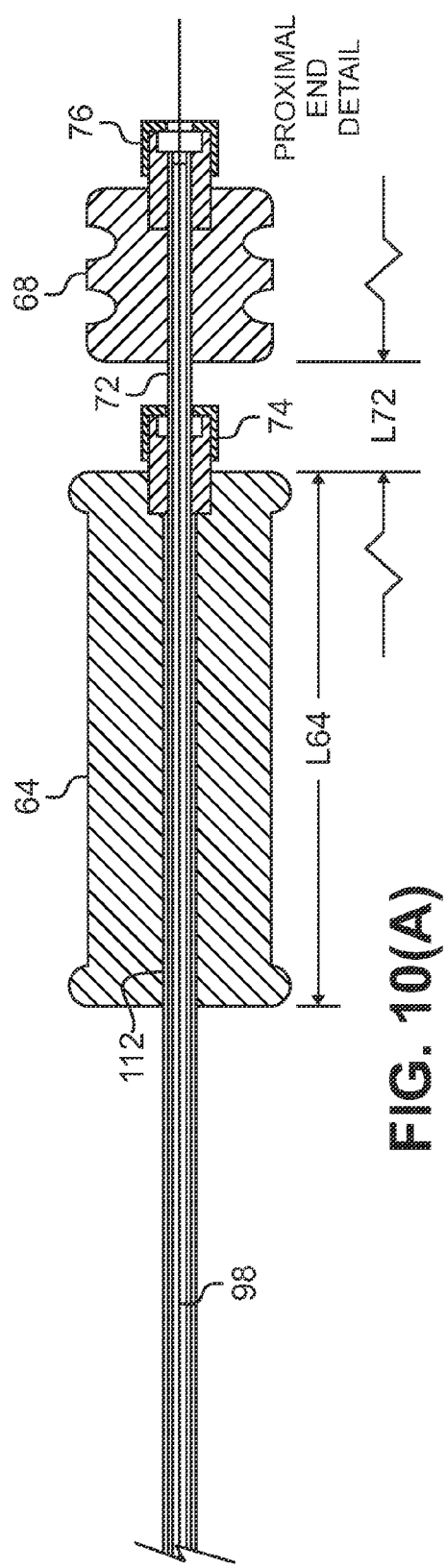
FIGS. 10(A)-(C) illustrate proximal end, distal end, and distal tip details of the device of FIG. 6.
Figure 10B:
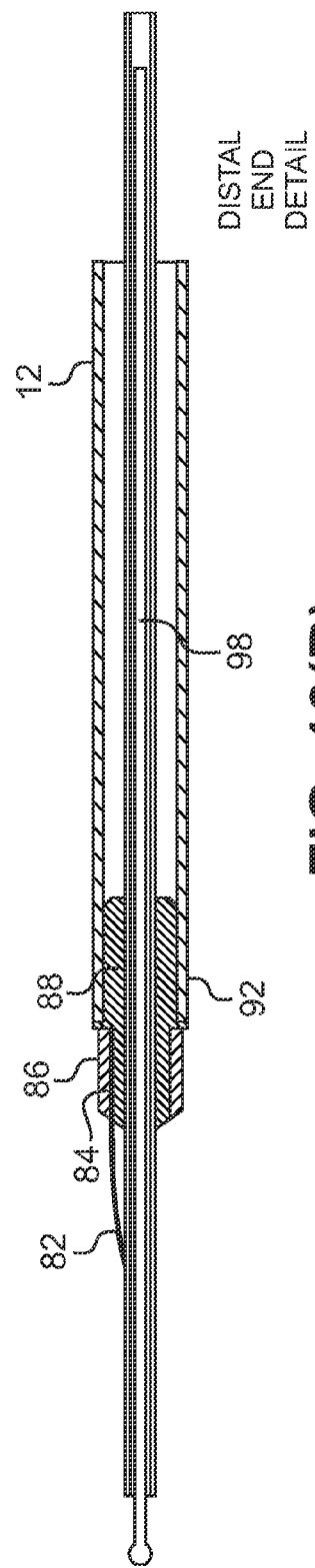
Figure 10C:
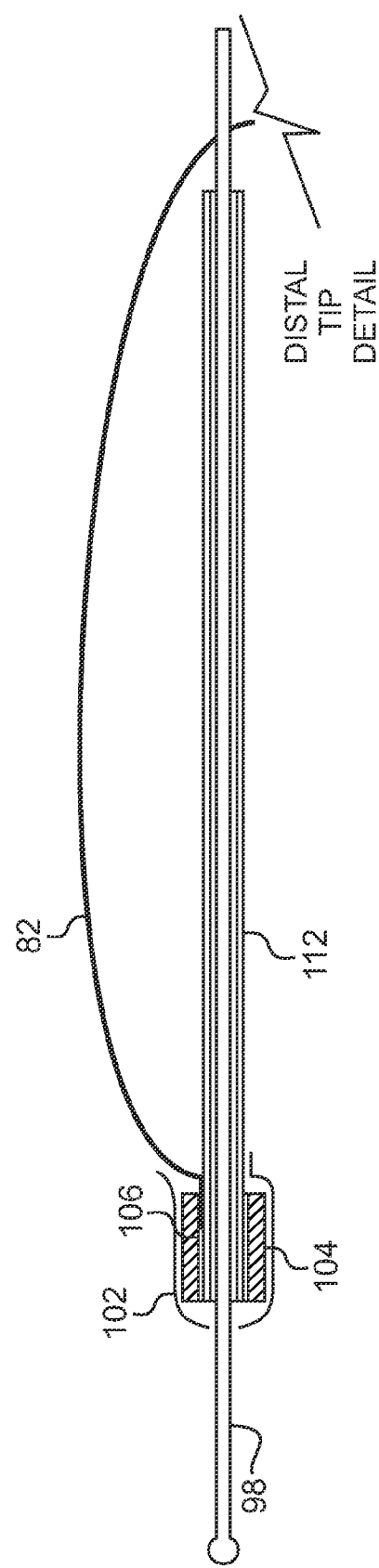

FIGS. 10(A)-10(C) illustrate a related embodiment, as well as various construction and manufacture details of a specific exemplary version. In these figures, a handle 64 includes a knob 68 which is separated by a distance L72. The distance L72 is chosen to allow for complete deployment of the implant device. A layer of epoxy 112 may seal the handle 64 to the sheath. Referring to FIG. 10(B), the sheath 98 is seen to terminate at a distal end at a distal end bushing 88. A hypo stock sleeve 86 surrounds a layer of epoxy 84 which is used to hold a NiTi tension band 82. The distal end bushing is coupled to the sheath 98 by a layer of epoxy 92. Referring to FIG. 10(C), greater detail is shown of the distal tip. In particular, a distal end of the NiTi tension band terminates at a hypotube 104 and is held in place by a layer of epoxy 106. A heat shrink 102 is set around the assembly.

Figure 12:
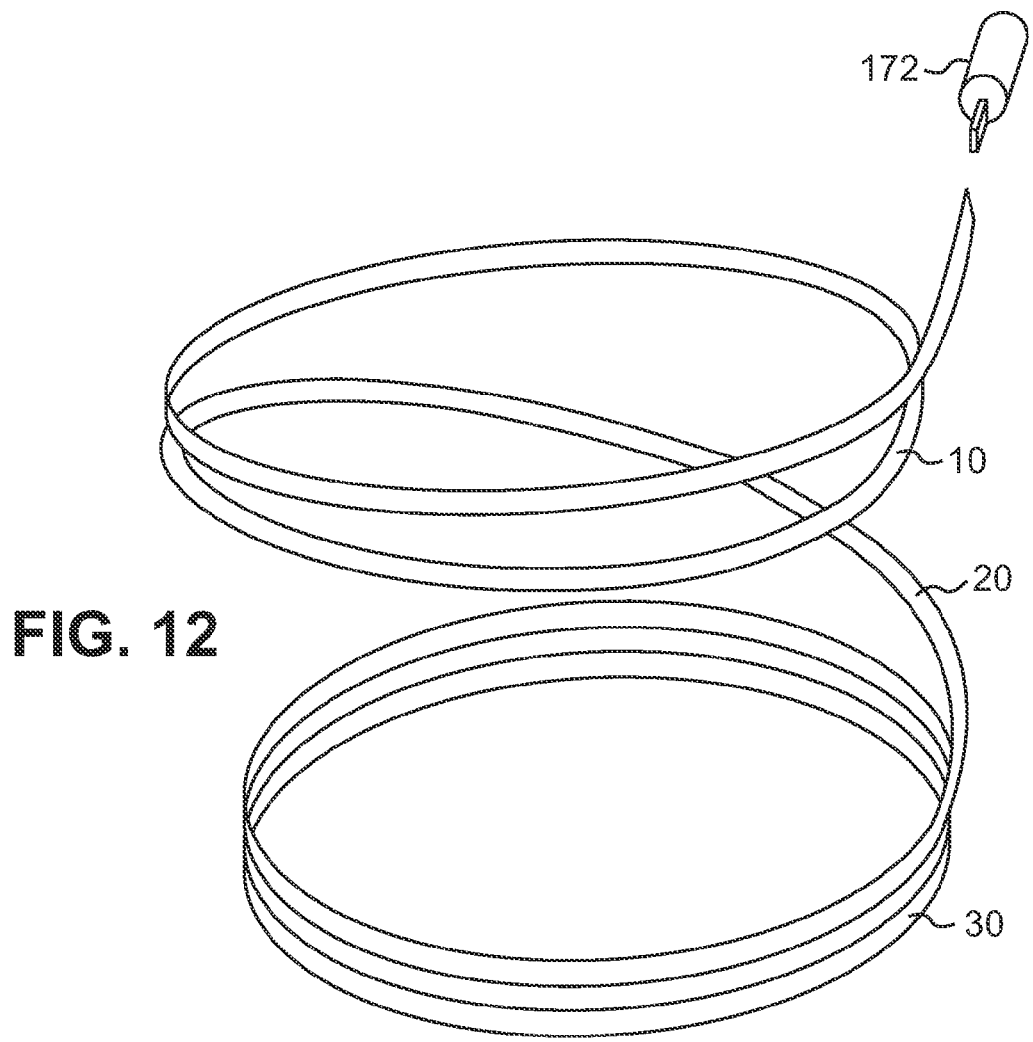
FIG. 12 illustrates removal of the implant device from a delivery device using a pusher and ratchet sleeve.
Figure 13:
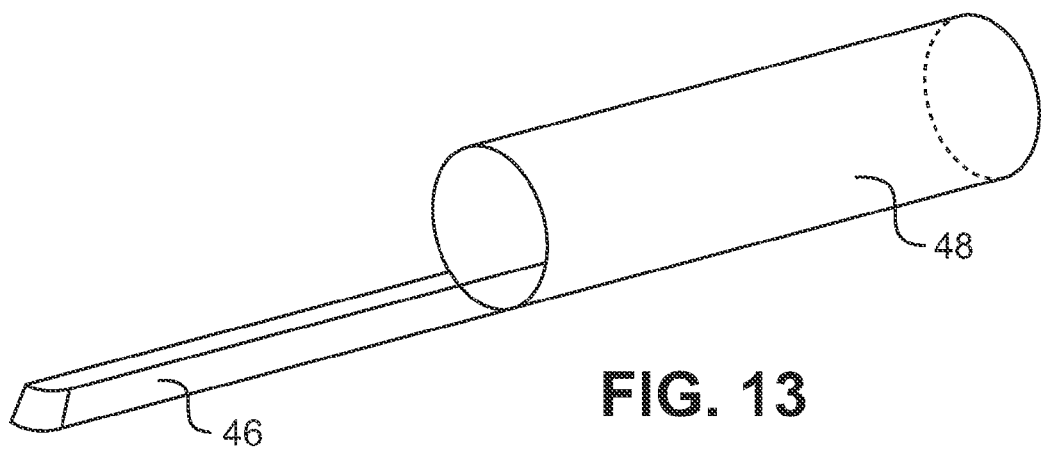
FIG. 13 illustrates a ratchet sleeve that may be employed to remove the implant device from a delivery device.

In a related implementation, as seen in FIGS. 12 and 13, the system may employ a small device, for example a ratchet sleeve having a cylinder 48 and extension 46 within the delivery catheter or sheath that can provide a ratcheting function. In this way, the handle may be simplified, and provided with greater control, by having the operator only have to provide a repeated short-stroke motion to controllably cause the implant device to exit the sheath and become implanted in the renal vessel.

The ratchet or ratcheting mechanism is shown in greater detail in FIG. 13 (not to scale). In particular, the ratchet sleeve is disposed within the sheath (it is exterior of the sheath for illustrative purposes in FIG. 12). Once the implant device is pulled back into the sheath, and the ratchet sleeve is disposed near the distal tip of the sheath, then the implant device may be deployed by repeatedly pushing it out of the tip, for example, a fraction of a centimeter, such as ¼ centimeter, to 2 inches, at a time. The implant device is prohibited against retracting into the sheath by virtue of the ratchet sleeve.

In a further related embodiment, a small balloon may be inflated within the ratchet sleeve if desired to provide a way for the ratchet sleeve to grab onto the implant device. By placing a tip of the implant device, for example, the proximal tip, into the ratchet sleeve, and inflating the balloon to fill up the interstitial space, the implant device may be effectively grabbed by being held between the balloon and the wall of the ratchet sleeve. In another embodiment, the inflation lumen and balloon may be provided in the pusher, and the device may be grabbed by inserting the pusher into the ratchet sleeve and inflating the balloon, thereby constricting the implant device tip in the same small diameter as the balloon (within the ratchet sleeve), causing the same to be grabbed. In yet another embodiment, a small balloon may be employed to render the volume within the ratchet sleeve closed, and in that case a small negative pressure may be pulled on the interior of the ratchet sleeve, constricting its walls and causing the same to pull inwards, grabbing onto the implant device in the process.

Figure 14A:
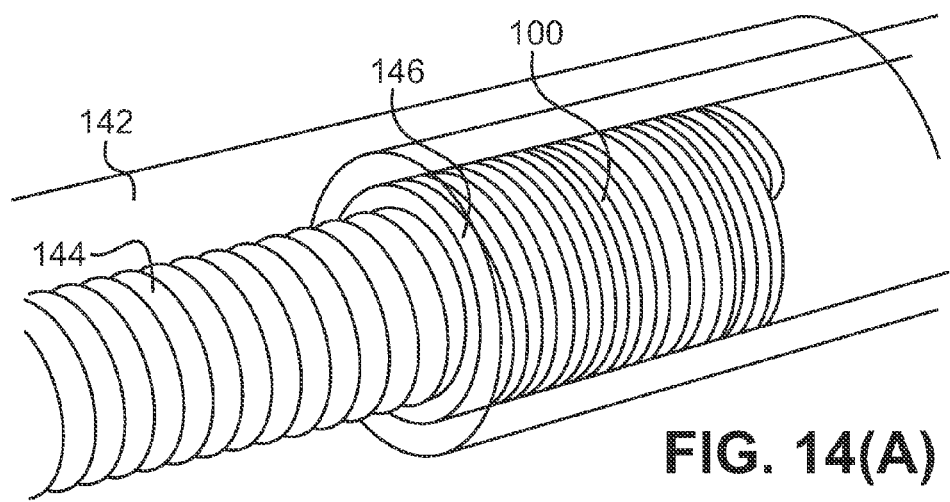
FIGS. 14(A)-(D) illustrate steps in removing the implant device from one embodiment of a delivery device, where the implant device expands off a mandrel.
Figure 14B:
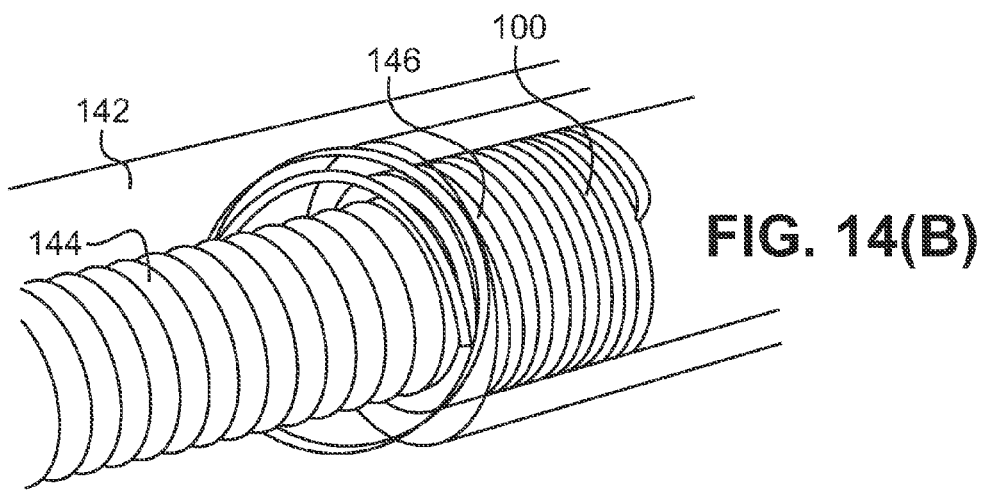
Figure 14C:
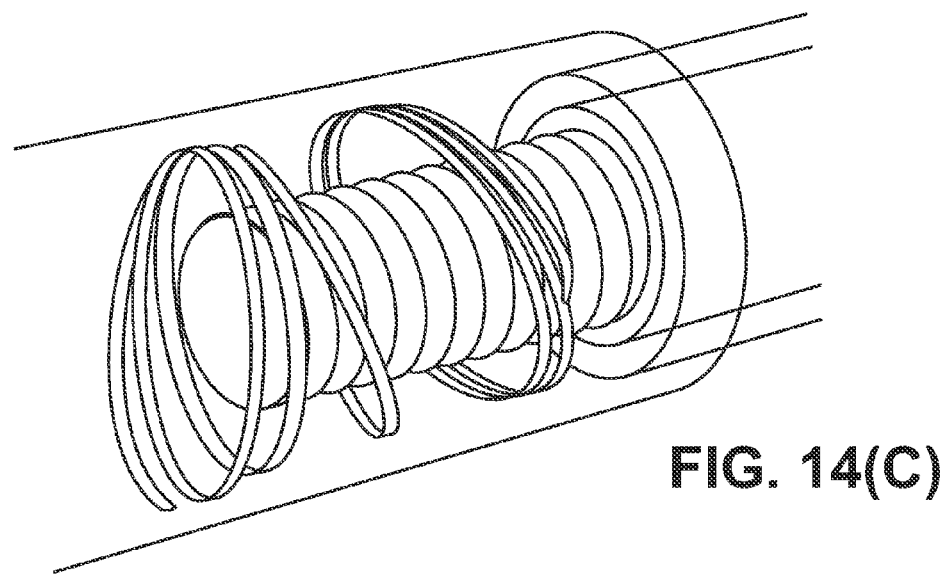
Figure 14D:
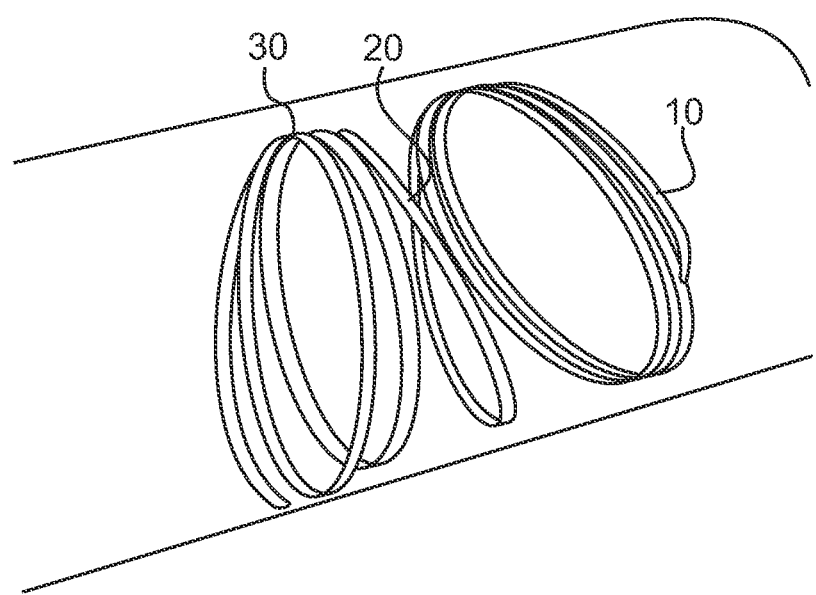

In an alternative implementation, illustrated in FIGS. 14(A)-14(C), the implant device 100 is coiled around a threaded mandrel 144 and confined by an outer tube 146. Removal of the outer tube allows the implanted device to spring away from the mandrel by virtue of its shape-memory character. FIGS. 14(A)-14(C) illustrate a sequence of deployment steps. In general, removing the outer tube causes immediate deployment, resulting in impingement of the device 100 against a vessel wall 142.

To deploy the distal end first, a split catheter shaft may be employed, such that separation of the catheter shaft at a location near the distal end causes the distal end to be deployed first. Of course, in certain implementations, the proximal end may also be deployed first. Such a split catheter shaft may be employed, for example, in the delivery of the implant device shown in FIGS. 14(A)-14(C). In this implementation, the distal end of the catheter may employ a polymer tip for atraumatic delivery, and the polymer tip may be radiopaque. As in most of the implementations described, the catheter may be delivered over a guide wire.

In another implementation, the distal end of the implant device is sutured to the catheter, and the wire of the device is wrapped around the catheter. In this connection it is noted that the implant device, during delivery, undeployed and constrained in a delivery device, may take the form of a straight wire, a helically-wrapped wire, or another configuration. The sutured end causes the distal end to be deployed last, and the final separation of the distal end from the catheter may be effected by way of cutting using a blade configured for that purpose, an electrical arc, or the like.

Referring to FIG. 16, the implant device 100 may also be held by the catheter by a grabber or grip 130, for example, a toothed grip. In particular, laser (or other) cuts 126 and 128 may be made in a distal cylindrical catheter tip to form a mouth or grip which may grab the proximal end of the implant device. In the figures, the laser cuts are made radially or longitudinally to the cylindrical axis of the grabber. It will be understood that curved cuts may also be employed, according to the needs of the particular application. The cuts allow bending or flexing away from the remainder 132 of the grabber or grabbing device 130. The mouth or grip may be configured, for example, via heat treatment (e.g., using a memory metal such as nitinol) or design or both, to distend or open when the mouth or grip is not confined by the sheath tube. Once the same is thus extended away from the sheath 96, the same may open and release the implant device 100.

Figure 16A:
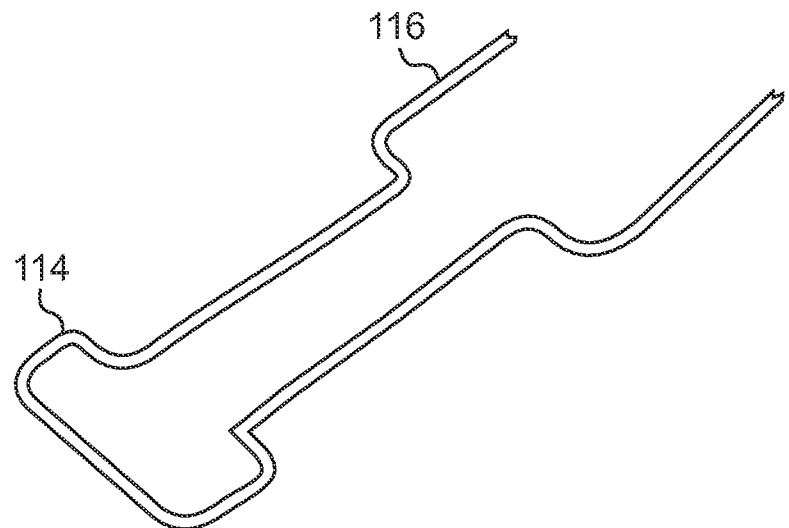
FIG. 16(A) illustrates a terminal end of an implant device, showing the end which may be grabbed by a grabber associated with the delivery device, or with a retrieval device.
Figure 16B:
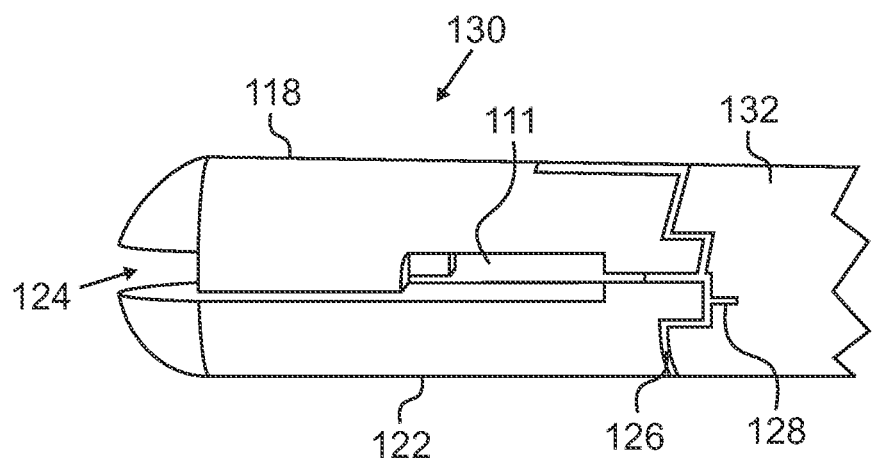
FIG. 16(B) illustrates the grabber associated with the delivery device, or with a retrieval device.
Figure 17A:
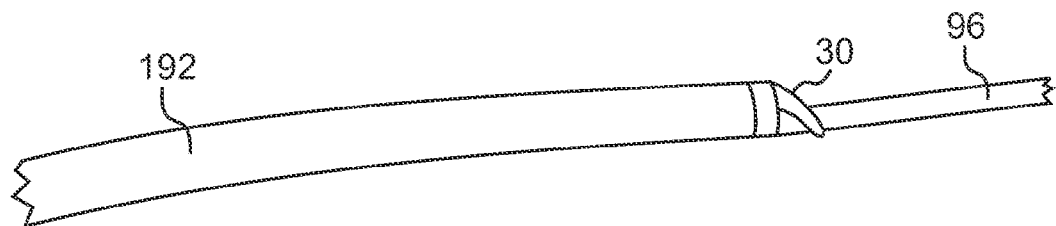
FIGS. 17(A)-(D) illustrate steps in removing the implant device from another embodiment of a delivery device, where the implant device is pushed out of a tube.
Figure 17B:
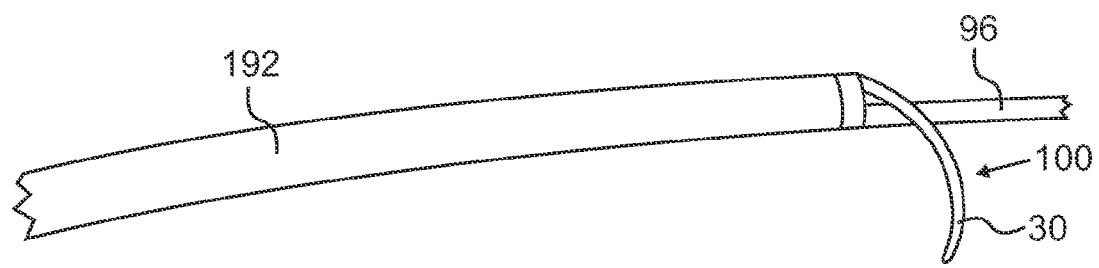
Figure 17C:
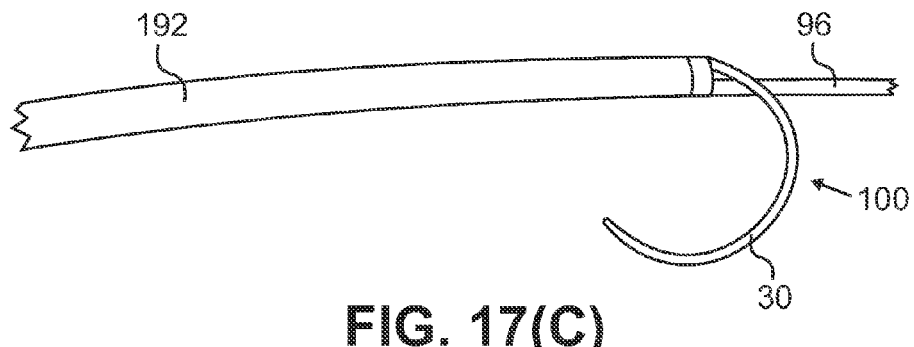
Figure 17D:
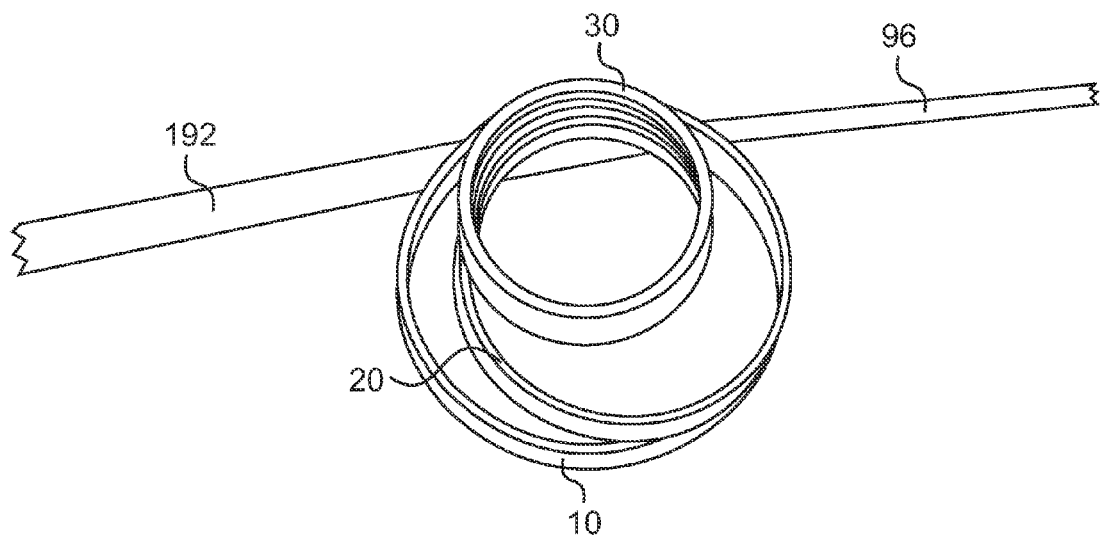

In a related implementation, the implant device may be formed with a groove between elements 114 and 116 (see FIG. 16(A)) or other feature to allow the grabber device 130 to hold the same in a secure and/or locked fashion. Similarly, the grabber device may have formed thereon a "tooth" 111 between upper half 118 and lower half 122 to allow additional points of contact (see FIG. 16(B)).

Figure 15A:
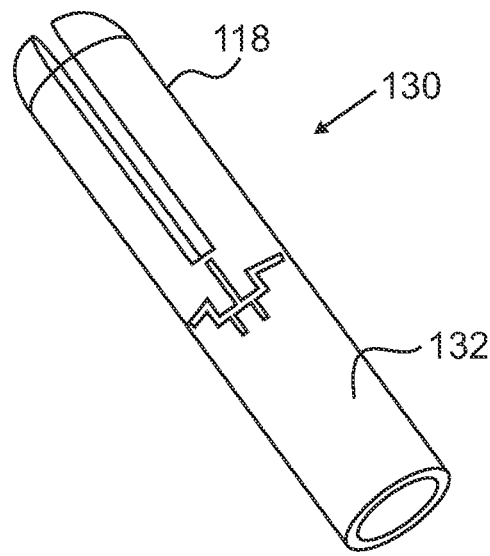
FIGS. 15(A) and (B) illustrate a grabber device, in both a closed and opened configuration, respectively.
Figure 15B:
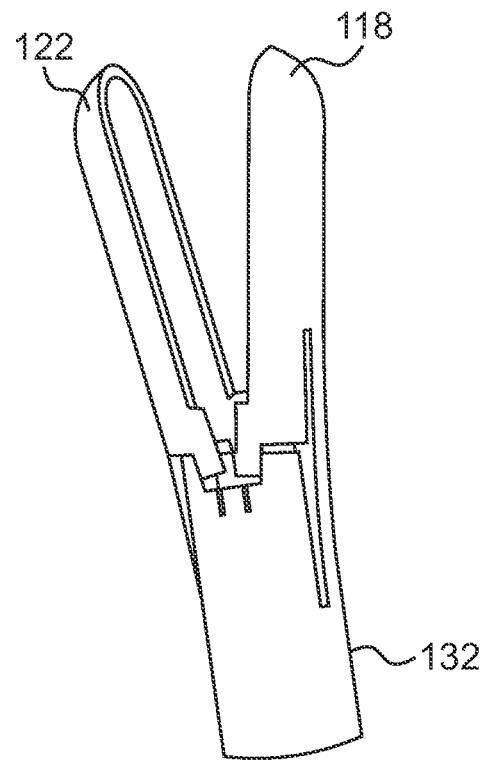
FIG. 15(C) illustrates a cutaway view of the grabber device in use within a delivery device.
Figure 15C:
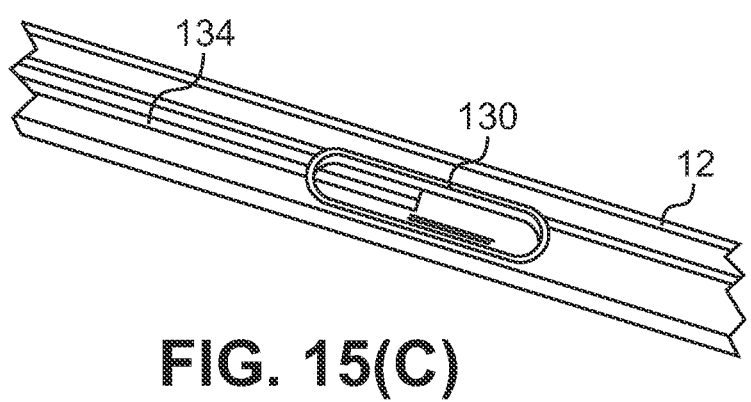

Additional views are also shown in FIGS. 15(A)-(C). In FIG. 15(C), a cutaway view of the grabbing device 130 is shown attached to a pusher 134 within the sheath 12.

In any case, when the grabbing device navigates the sheath or delivery catheter, it must navigate both curved sections and straight sections. In some systems, it may be advantageous to provide the same with a small curve or with additional laser cuts to allow the grabber device a degree of flexibility.

FIGS. 17(A)-(D) illustrate another embodiment, which deploys the implant device perpendicular to the direction of implantation of the exemplary embodiment shown in FIGS. 14(A)-14(D). This deployment direction may be useful in certain patient anatomies. In this embodiment, the shape-memory character of the implant device may be employed to allow the same to be delivered from the end of a straight tube. As will be seen, one ring deploys prior to the other. In some cases, it may be necessary to reposition the implant device if the same does not deploy properly directly out of the tube. In FIGS. 17(A)-(D), the implant device 100 emerges directly (and initially linearly) out of the distal tip of the catheter 192. In FIGS. 17(A)-(D), the distal ring 30 emerges first, followed by the proximal ring 10, though it will be understood that the order may be reversed.

In general, the delivery system will have distal and proximal ends, where the distal end employs an atraumatic distal tip and the proximal end includes a handle. The system further includes a catheter shaft having a tubular structure traversing from the proximal end to the distal end. The guide wire lumen includes a luminal space to enable passage of a range of guide wire sizes. In one implementation, the guide wire lumen is further capable of being advanced distally or proximally to enable deployment of the ring-like coil implant device attached along the external surface of the guide wire lumen and contained within the inner surface of the outer catheter shaft. As in some embodiments above, the delivery system catheter may employ a flexible distal segment and a steering wire anchored at the distal portion of the delivery catheter.

In some implementations, the deployment device, or another device, may allow a degree of recapture to occur in order to fix incorrect implanted device placements within the vessel. For example, where the device is pushed through a tube for deployment, the same two may be used to deliver a small wire equipped with maneuverable jaws at its distal end. For example, a modified guide wire may be employed. A control wire running alongside the guide wire may allow the contraction of one or more jaws in order to grab an errant device. If desired, retraction of the guide wire may then allow the complete removal of the implanted device. In the system described above where a mouth or grip is closed or opened by virtue of its being enclosed by a sheath or not, respectively, the mouth or grip may be employed to recapture an implanted device. In the same way, the ratchet sleeve with incorporated balloon may provide this function as well.

Figure 18A:
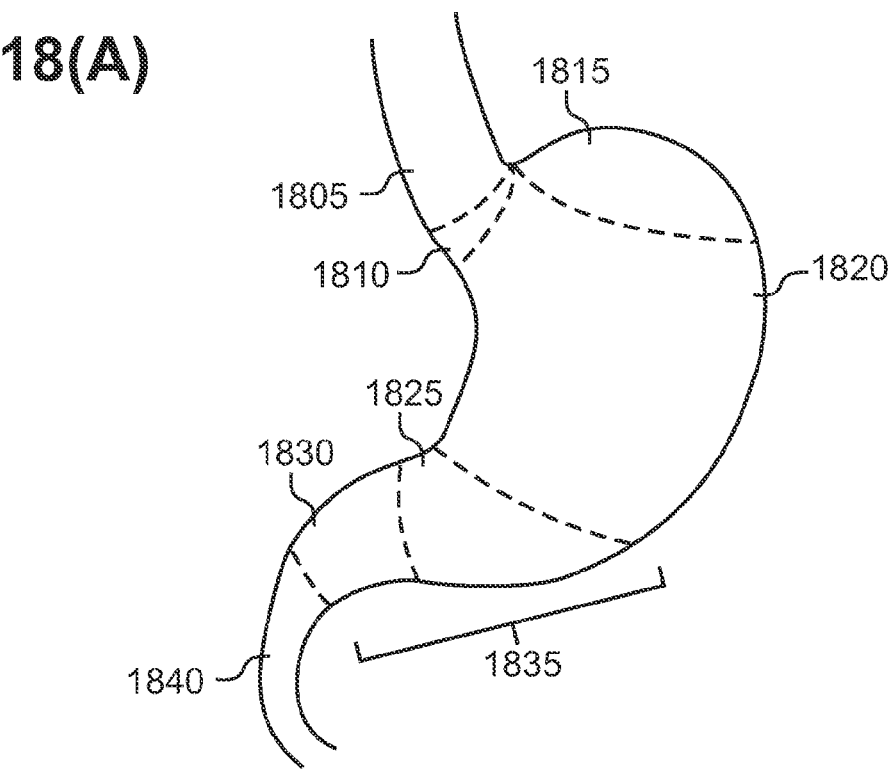
FIGS. 18(A) and (B) show an illustrative anatomy of a patient's stomach.
Figure 18B:
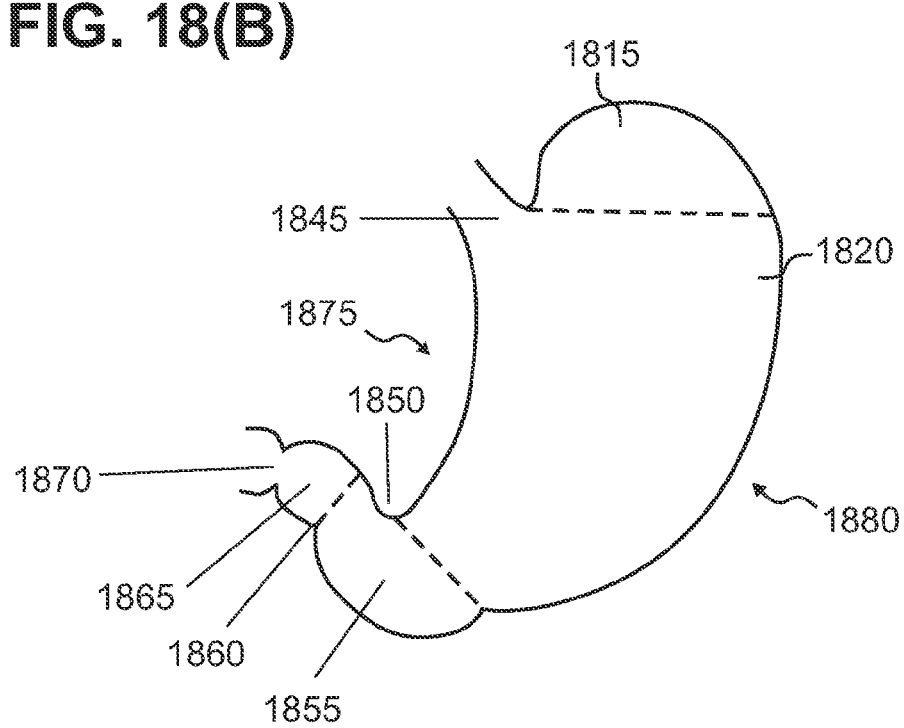

In another embodiment, a similarly shaped ring system may be employed to treat diabetes in patients. The anatomy of the stomach is illustrated in FIGS. 18(A) and (B). Shown are the esophagus 1805, cardia 1810, fundus 1815, body 1820, antrum 1825, pylorus 1830, mucous glands 1835, and duodenum 1840. FIG. 18(B) also shows the antrum cadiacum 1845, incisura angularis 1850, pyloric part 1855, sulcus intermedius 1860, pyloric antrum 1865, pyloroduodenal opening 1870, lesser curvature 1875, and greater curvature 1880. It is noted that, historically, some patients who were treated for obesity using the technique of gastric bypass had a surprising benefit of being treated or even cured of their diabetes.

It is believed that the placement of the ring system in a location at the lower end of the esophagus, towards the cardia, may in some cases treat diabetes in the same way. In this case, the ring system would simply be deployed down the esophagus. The ring system itself may have a larger diameter with a wider ribbon, and may deliver higher radial forces. Higher radial forces may be achieved by use of a thicker ribbon as well.

In general, it is noted that any body cavity with a substantially cylindrical shape may benefit from application of the system and method disclosed, if that body cavity benefits from pressure application.

Mechanism of Operation

A single or dual ring system, as well as the helix or helical extension arms, may compress tissue, to cause a narrowing of certain channels within the tissue. For example, sodium, calcium, or potassium channels may be blocked by mild compression. It is believed that a suitable amount of force will result in a compression of the first one to five cellular layers in the tissue. In particular, it may be important to at least compress the first layer.

It is believed that the amount of pressure necessary should be more than 10 g/mm² (for example, greater than 20 g/mm²), but less than 340 g/mm² (for example, less than about 200 g/mm²), as noted above. While it may be desired to have the rings and helix or helices exert a relatively constant force around the circumference of the vessel, it is more likely, given anatomical imperfections, that certain areas will receive more pressure than others. However, compliance of the ring and the use of the helix helps to distribute forces around the implant device. In general it is believed that the amount of pressure needed will primarily be a function of the material used, the diameter of the artery or vein, and the thickness of the muscle sleeve.

It is also noted that the ring may cause the vessel in which it dwells to become more oval or round, or otherwise to maintain a more open shape than that which it adopted before, in the absence of the implant device. In this way, the device acts as a stent, enhancing patency, hemodynamics and the resulting blood flow. The device affects the shape of the vessel, and vice-versa. This effect improves apposition of the implant device to improve outcomes by enabling circumferential contact resulting in laminar blood flow, and can help to treat stenotic vessels. One aspect of the device that assists in this regard is the device ring compliance, which causes the device to conform to the vessel—i.e., the radial expansion helps to keep the device in place in a dynamic way.

In some implementations, the metallic nature of the implanted device may be employed to provide a level of active heating so as to heat or necrose tissue adjoining the implant device. For example, such heating may be by way of induction using a device external to the patient. The device may be caused to heat the implant device and thus heat (and treat) the tissue creating localized necrosis, and then be easily removed from the vicinity of the patient to stop the heating. In advanced versions of this implementation, the heating device and the implant device may be tuned such that only one implant device is heated at a time, if multiple implant devices have been deployed.

The mechanism of operation of the device, where the same is disposed in the esophagus is described above in the sections describing their deployment.

Construction

As will be understood, the rings and helices may be constructed of several types of materials. For example, biocompatible metals such as nitinol may be employed, and the same exhibit useful shape memory properties. Biocompatible polymers or elastomers may also be employed.

Figure 19:
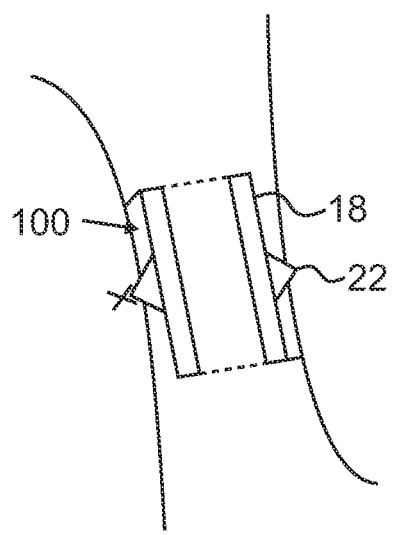
FIG. 19 illustrates a feature that may be employed in certain implementations of the implant device.

The ring may employ a shoulder 18 for stability, as well as a feature 22 to cause pressure, as illustrated in FIG. 19. For example, the feature 22 to cause pressure may be any three-dimensional solid capable of exerting additional pressure along a predetermined area, such as a ridge. The portion of the shoulder adjacent to tissue may be roughened or otherwise treated in order to provide an irritant to that tissue, so as to cause endothelialization as discussed above. Such endothelial cells are typically not conductive, and thus act as a long-term-care modality.

Coatings

While not required in all implementations, various coatings or other agents may be applied or made part of the rings and/or helices, such coatings or agents capable of disrupting the propagation of aberrant electrical signals or otherwise treating arrhythmias. Such coatings may include drugs, biologics, chemicals, or combinations, that by themselves or in combination with the mechanical compression act as a treatment for hypertension. As another example, the rings and helices may be coated with tantalum, for example, a 3-5 micron coating.

The implant device may be permanent, removable, or the same may be configured and designed to be absorbed into the body after a period of time. In a removable embodiment, a removable portion (which may be the entire implant device or a portion thereof) may be installed for a period of time, for example, between 30 minutes and 24 hours, and then removed.

Variations

Other aspects of the invention may include one or more of the following. The device may include a contiguous circumferential ring normally perpendicular to the ostium of the vessel, and the ring or coil structure may have at least one full rotation, as well as a pitch that is >1° from the first ring. The ring or coil structure may provide radial support to stenosed vessels. The ring or coil structure may employ a single ring (with one or more coils or windings) or may have both a distal ring and a proximal ring. The proximal ring may employ a single extension arm or a plurality of extension arms that extend distally toward and connect to the distal ring. The extension arms may have a helical shape and may extend distally toward the distal ring. The ring or coil structure may apply mechanical pressure to tissue. The ring or coil structure may have a material composition, surface treatment, coating, or biological agent and/or drug to cause a human biological response, for example, intimal hyperplasia or endothelization, in a controlled or semi-controlled way in order to cause a desired effect. The ring or coil structure may have at least one full circumferential winding, and indeed more, and may include a helical extension moving distally from the outer diameter of the first ring and terminating within the vessel to prevent migration of the coil or ring structure. The ring or coil may be made of a round wire or ribbon profile that is shaped into a ring or coil. The ring or coil may have various cross-sectional shapes designed to focus mechanical force in a circumferential or helical pattern against the inner surface of a vessel or structure. These shapes include but are not limited to round or circular, triangular, rectangular, "U" shaped, or any number of other shape combinations. The ring or coil structure may have a material composition and/or geometry designed to sufficiently conform to tissue to prevent coagulation or thrombus, and may include a material coating to further reduce or prevent such coagulation or thrombus. The ring or coil structure may have a hexagonal, pentagonal, and/or octagonal shape when viewing in an end view. This geometric shape may be designed to improve conformability to the vessel following implantation. By changing the geometry of the loop or ring, the ring and vessel may be mutually conformed, and the radial force equalized along the circumference of the inner surface of the vessels. The ring or coil structure may have the above-noted shapes at the proximal end but may employ a circular shape at the distal end.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed:

1. A method for treating hypertension in a human patient, the method comprising the steps of:
    choosing a size of an implant device for insertion into a renal vasculature of the patient, the implant device comprising a single coiled ribbon wire having a proximal circumferential ring, a distal circumferential ring, and an extension arm connecting the proximal ring to the distal ring, wherein a plane of the proximal and distal circumferential rings are substantially perpendicular to the axis of the implant device;

inserting the ribbon wire into the renal vasculature of the patient in an uncoiled and substantially linear configuration within a delivery catheter;

advancing the uncoiled ribbon wire from a distal tip of the delivery catheter and coiling the proximal and distal circumferential rings within the renal vasculature, the proximal and distal circumferential rings providing radial outward compressive force along a circumference of the renal vasculature at each proximal and distal circumferential ring location along a portion of the renal vasculature; and abrogating or lessening overactivity of the patient's renal sympathetic nervous system by the outward compressive force of the proximal and distal rings against the renal vasculature.

2. The method of claim 1, wherein a diameter of the proximal ring is greater than the diameter of the distal ring.

3. The method of claim 1, wherein a diameter of the proximal ring is substantially the same as the diameter of the distal ring.

4. The method of claim 1, wherein in an undeployed configuration the diameter of the proximal ring is between about 4 to 60 mm and the diameter of the distal ring is between about 6 to 60 mm.

5. The method of claim 4, wherein the diameters of the proximal ring and the distal ring are approximately 15 mm.

6. The method of claim 4, wherein the diameter of the proximal ring is substantially 25 mm and the diameter of the distal ring is substantially 15 mm.

7. The method of claim 1, wherein in a deployed configuration the diameter of the proximal ring is between about 2 to 40 mm and the diameter of the distal ring is between about 3 to 40 mm.

8. The method of claim 1, wherein the proximal and distal rings are chosen such that at least one ring is 10-50% oversized compared to a vessel in which the implant device is implanted.

9. The method of claim 1, wherein the ring is configured to, when deployed, deliver a force against adjacent tissue of between about 0.5 g/mm$^2$ and 340 g/mm$^2$.

10. The method of claim 9, wherein the ring is configured to, when deployed, deliver a force against adjacent tissue of between about 20 g/mm$^2$ and 200 g/mm$^2$.

11. The method of claim 1, wherein the proximal ring is configured to deliver a lesser force when deployed against adjacent tissue than the distal ring.

12. The method of claim 1, wherein the rings are configured to deliver a force against adjacent tissue when the implant device is deployed of between about 5 g/mm$^2$ and 340 g/mm$^2$.

13. The method of claim 1, wherein the rings configured to deliver a force against adjacent tissue when the implant device is deployed of between about 20 g/mm$^2$ and 200 g/mm$^2$.

14. The method of claim 1, wherein the force is sufficient to cause necrosis or apoptosis in the adjacent tissue, the necrosis or apoptosis sufficient to block or delay electrical conduction.

15. The method of claim 1, wherein an extremity of a ring is shaped to increase frictional or mechanical resistance against movement.

16. The method of claim 1, wherein the implant device is coated with a material composition, surface treatment, coating, or biological agent and/or drug.

17. A method for treating hypertension in a human patient, the method comprising the steps of:

choosing a size of an implant device for insertion into a renal vasculature of the patient, the implant device comprising a single coiled ribbon wire having proximal and distal circumferential rings substantially perpendicular to the axis of the implant device connect by an extension arm, each ring having at least one winding of the ribbon wire;

inserting the ribbon wire into the renal vasculature of the patient in an uncoiled and substantially linear configuration within a delivery catheter;

advancing the uncoiled ribbon wire from a distal tip of the delivery catheter and coiling the proximal and distal circumferential rings within the renal vasculature so that the proximal and distal circumferential rings assume a radially deployed orientation, the proximal and distal circumferential rings providing radial outward compressive force on adjacent tissue of the renal vasculature at each proximal and distal circumferential ring location; and blocking or delaying electrical signals traveling along the axis of the renal vasculature by the compressive force of the proximal and distal rings against the adjacent tissue to thereby cause one or more renal nerves associated with the renal vasculature to be at least partially denervated.

18. The method of claim 17 further including a step of applying thermal energy through the implant device to adjacent tissue using inductive heating.

19. The method of claim 17 further including a step of ablating surrounding tissue through application of heat or RF emissions.

20. The method of claim 17 further including a step of applying cryothermia therapy.

21. A method for treating hypertension in a human patient, the method comprising the steps of:

inserting an undeployed implant device in an uncoiled and substantially linear configuration within a delivery catheter into the patient through a blood vessel, the implant device having a shape when coiled comprising a single ribbon wire having proximal and distal circumferential rings substantially perpendicular to the axis of the implant device connect be an extension arm, the proximal and distal rings having at least one circumferential winding of the ribbon wire;

positioning the implant device adjacent to a renal nerve of at least one kidney of the patient;

deploying the uncoiled and substantially linear ribbon wire from the distal tip of the delivery catheter and coiling the proximal and distal circumferential rings within the blood vessel so that the proximal and distal circumferential rings exert a radially outward circumferential force to a portion of the blood vessel at each proximal and distal ring location; and de-stimulating or at least partially denervating the renal nerve by the radially outward circumferential force of the proximal and distal rings against the blood vessel.

22. A method of implementing catheter-based renal denervation in a human patient having a renal artery, the method comprising the steps of:

delivering an undeployed implant device using a catheter inserted in the patient's femoral artery, the undeployed implant device being uncoiled and arranged in the catheter in a substantially linear configuration and having a shape when deployed comprising a single coiled ribbon wire having proximal and distal circumferential rings connect by an extension arm, wherein a plane of the proximal and distal circumferential rings are substantially perpendicular to the axis of the implant device;

advancing the catheter so that the implant device is positioned at a selected location in the renal artery;

deploying the uncoiled and substantially linear ribbon wire from the catheter tip, the proximal and distal circumferential rings coiling so that the proximal and distal circumferential rings exert a radially outward circumferential force along at each proximal and distal ring location; and denervating portions of efferent sympathetic renal nerves or sensory afferent renal nerves encasing the renal artery by the radially outward circumferential force of the proximal and distal rings against the renal artery so as to cause a reduction in sympathetic nervous system drive.

23. A method of treating a malady, the method comprising the steps of:

delivering an undeployed implant device using a catheter inserted in a patient, the undeployed implant device being uncoiled and arranged in the catheter in a substantially linear configuration and having a shape when deployed comprising a single coiled ribbon wire having proximal and distal contiguous circumferential rings substantially perpendicular to the axis of the implant device connect by an extension arm, the proximal and distal rings having at least one winding of a ribbon wire;

advancing the catheter so that the implant device is positioned at a targeted selected location in the patient's anatomy; and deploying the uncoiled and substantially linear ribbon wire from the catheter tip, the ribbon wire coiling so that the proximal and distal circumferential rings exert a radially outward circumferential force along at each proximal and distal ring location; and partially blocking electrical signals traveling along the targeted location or to at least partially denervating along the circumference at the proximal and distal ring locations by the outward compressive force of the proximal and distal rings against the selected location.

24. The method of claim 23, wherein the targeted location comprises the patient's stomach and the catheter is fed through the patient's esophagus.

25. The method of claim 23, wherein the targeted location comprises a distal renal artery and the catheter is fed through the patient's femoral artery.

* * * * *